US011318200B2

(12) United States Patent
Dominowski et al.

(10) Patent No.: US 11,318,200 B2
(45) Date of Patent: May 3, 2022

(54) METHODS AND COMPOSITIONS FOR INDUCTION OF IMMUNE RESPONSE

(71) Applicant: Zoetis Services LLC, Parsippany, NJ (US)

(72) Inventors: Paul Joseph Dominowski, Kalamazoo, MI (US); Duncan Mwangi, Kalamazoo, MI (US); Joseph M. Bricker, Kalamazoo, MI (US); Dennis L. Foss, Kalamazoo, MI (US); Sharath K. Rai, Kalamazoo, MI (US); Suman Mahan, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 15/039,733

(22) PCT Filed: Nov. 21, 2014

(86) PCT No.: PCT/US2014/066767

§ 371 (c)(1),
(2) Date: May 26, 2016

(87) PCT Pub. No.: WO2015/080959

PCT Pub. Date: Jun. 4, 2015

(65) Prior Publication Data

US 2018/0008701 A1 Jan. 11, 2018

Related U.S. Application Data

(60) Provisional application No. 61/909,045, filed on Nov. 26, 2013.

(51) Int. Cl.
| *A61K 39/39* | (2006.01) |
| *A61K 39/00* | (2006.01) |
| *A61K 31/704* | (2006.01) |
| *A61K 45/06* | (2006.01) |
| *A61K 31/14* | (2006.01) |
| *A61K 31/575* | (2006.01) |
| *A61K 31/7028* | (2006.01) |

(52) U.S. Cl.
CPC ............ *A61K 39/39* (2013.01); *A61K 31/14* (2013.01); *A61K 31/575* (2013.01); *A61K 31/704* (2013.01); *A61K 31/7028* (2013.01); *A61K 45/06* (2013.01); *A61K 2039/545* (2013.01); *A61K 2039/55511* (2013.01); *A61K 2039/55555* (2013.01); *A61K 2039/55561* (2013.01); *A61K 2039/55572* (2013.01); *A61K 2039/55577* (2013.01)

(58) Field of Classification Search
None
See application file for complete search history.

(56) References Cited

U.S. PATENT DOCUMENTS

| 8,580,280 | B2 * | 11/2013 | Dominowski | ..... A61K 39/0011 424/278.1 |
| 9,623,099 | B2 * | 4/2017 | Crump | ............... A61K 39/0216 |
| 9,662,385 | B2 * | 5/2017 | Dominowski | ..... A61K 39/0011 |
| 10,238,736 | B2 * | 3/2019 | Dominowski | ..... A61K 39/0011 |
| 2005/0208614 | A1 | 9/2005 | Kline | |
| 2005/0220814 | A1 * | 10/2005 | Dominowski | ..... A61K 39/0225 424/204.1 |
| 2005/0244505 | A1 | 11/2005 | Higbee | |
| 2006/0057700 | A1 | 3/2006 | Castric | |
| 2009/0324641 | A1 * | 12/2009 | Dominowski | ..... A61K 39/0011 424/207.1 |
| 2013/0084306 | A1 * | 4/2013 | Davis | ................... A61K 39/099 424/196.11 |
| 2013/0302369 | A1 * | 11/2013 | Abdelmagid | ........ A61K 39/099 424/201.1 |
| 2014/0056940 | A1 * | 2/2014 | Dominowski | ..... A61K 39/0011 424/209.1 |
| 2015/0140034 | A1 * | 5/2015 | Dominowski | ........ A61K 39/002 424/203.1 |
| 2016/0256540 | A1 * | 9/2016 | Ons | ........................ A61K 39/12 |
| 2017/0304430 | A1 * | 10/2017 | Tani | ..................... A61K 39/165 |
| 2018/0008701 | A1 * | 1/2018 | Dominowski | .......... A61K 45/06 |
| 2018/0021424 | A1 * | 1/2018 | Dominowski | .......... A61K 39/12 |
| 2019/0008953 | A1 * | 1/2019 | Dominowski | ..... A61K 39/0011 |
| 2021/0338810 | A1 * | 11/2021 | Dominowski | ..... A61K 39/0258 |

OTHER PUBLICATIONS

Barr et al, Advanced Drug Delivery Reviews, 1998, 32:247-271 (Year: 1998).*
Bonam et al, Trends in Pharmacological Sciences, Sep. 2017, 38/9:771-793 (Year: 2017).*
Dominowski, Dissertation Abstracts International, 2008, 69/12, suppl. B, 213, abstract only (Year: 2008).*
Kim et al, Avian Sciences, 2012, 56/1:97-109. published ahead of print Sep. 18, 2011 (Year: 2012).*
Pridgeon et al, Vet. Immunol. and Immunopathol., 2012, 145:179-190. (Year: 2012).*
Ridpath et al, Vet. Res. Commun., 2010, 34:691-702. published online Sep. 28, 2010 (Year: 2010).*
Slvakumar et al, Saudi Pharmaceutical Journal. 2011. 19:197-206. available online Jun. 25, 2011 (Year: 2011).*
Bertani et al, EcoSal Plus 2018; doi:10.1128/ecosalplus.ESP-001-2018. 19 pages (Year: 2018).*
Freudenberg et al., "Role of lipopolysaccharide susceptibility in the innate immune response to *Salmonella typhimurium* infection: LPS, a primary target for recognition of Gram-negative bacteria," Microbes and Infection 3(14-15): pp. 1213-1222 (2001).

(Continued)

*Primary Examiner* — Nita M. Minnifield
(74) *Attorney, Agent, or Firm* — Vyacheslav Vasilyev (57) ABSTRACT

The invention provides a substantially antigen-free composition for induction of innate immune response in a bird or a mammal, the composition comprising a saponin, a sterol, a quaternary amine, and a polyacrylic polymer to the mammal or bird. Methods of using the composition are also provided.

16 Claims, 1 Drawing Sheet

Specification includes a Sequence Listing.

(56) References Cited

OTHER PUBLICATIONS

Skovbjerg et al., "Gram-Positive and Gram-Negative Bacteria Induce Different Patterns of Cytokine Production in Human Mononuclear Cells Irrespective of Taxonomic Relatedness," J Interferon Cytokine Res. 30(1): 23-32 (2010).

Preston, A. et al., "Complete Structures of Bordetella bronchiseptica and Bordetella parapertussis Lipopolysaccharides*," The Journal of Biological Chemistry vol. 281, No. 26, pp. 18135-18144, Jun. 30, 2006.

Banemann, A. et al., "The Lipopolysaccharide of Bordetella bronchiseptica Acts as a Protective Shield against Antimicrobial Peptides," Infection and Immunity, Dec. 1998, pp. 5607-5612, vol. 66, No. 12.

Bache, C. et al., "Bordetella Pertussis Toxin does not induce the release of pro-inflammatory cytokines in human whole blood," Med. Microbiol. Immunol. (2012) 201: 327-335.

Gallego, C. et al., "Interaction of Bordetella bronchiseptica and Its Lipopolysaccharide with in Vitro Culture of Respiratory Nasal Epithelium," Hindawi Publishing Corporation Veterinary Medicine International, vol. 2013, Article ID 347086, 9 pages, http://dx.doi.org/10.1155/2013/347086.

Kubler-Kielb, J. et al., "Oligosaccharide conjugates of Bordetella pertussis and bronchiseptica induce bactericidal antibodies, an addition to pertussis vaccine," PNAS, Mar. 8, 2011, vol. 108,| No. 10 , pp. 4087-4092.

Love, C. F. "The Role of Bps Polysaccharide in Bordetella Resistance to Host Innate Defenses," A Dissertation Submitted to the Graduate Faculty of Wake Forest University Graduate School of Arts and Sciences, Microbiology and Immunology, Aug. 2010, Winston-Salem, North Carolina.

Chalker, V.J., et al., "Respiratory Disease in Kennelled Dogs: Serological Responses to Bordetella bronchiseptica Lipopolysaccharide Do Not Correlate with Bacterial Isolation or Clinical Respiratory Symptoms," Clinical and Diagnostic Laboratory Immunology, May 2003, pp. 352-356 vol. 10, No. 3.

* cited by examiner

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 1
tcgtcgacga tcggcgcgcg ccg                                               23

<210> SEQ ID NO 2
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 2
tcgacgtcga tcggcgcgcg ccg                                               23

<210> SEQ ID NO 3
<211> LENGTH: 24
<212> TYPE: DNA
<213> ORGANISM: Artificial Sequence
<220> FEATURE:
<223> OTHER INFORMATION: CpG oligonucleotide

<400> SEQUENCE: 3
tcgacgtcga tcggcgcgcg ccgt                                              24

<210> SEQ ID NO 4
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Iodo-2'-deoxyuridine
<220> FEATURE:
<221> NAME/KEY: misc_feature
<222> LOCATION: (1)..(1)
<223> OTHER INFORMATION: n is a, c, g, or t

<400> SEQUENCE: 4
ncgacgtcga tcggcgcgcg ccg                                               23

<210> SEQ ID NO 5
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Iodo-2'-deoxyuridine
<220> FEATURE:
<221> NAME/KEY: misc_feature
<222> LOCATION: (1)..(1)
<223> OTHER INFORMATION: n is a, c, g, or t

<400> SEQUENCE: 5
ncgacgtcga tcggcgcgcg ccgt                                              24
```

-continued

```
<210> SEQ ID NO 6
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Iodo-2'-deoxyuridine
<220> FEATURE:
<221> NAME/KEY: misc_feature
<222> LOCATION: (1)..(1)
<223> OTHER INFORMATION: n is a, c, g, or t

<400> SEQUENCE: 6
ncgacgtcga tcggcgcgcg ccgt                                          24

<210> SEQ ID NO 7
<211> LENGTH: 23
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Ethyl-2'-deoxyuridine
<220> FEATURE:
<221> NAME/KEY: misc_feature
<222> LOCATION: (1)..(1)
<223> OTHER INFORMATION: n is a, c, g, or t

<400> SEQUENCE: 7
ncgacgtcga tcggcgcgcg ccg                                           23

<210> SEQ ID NO 8
<211> LENGTH: 24
<212> TYPE: DNA
<213> ORGANISM: Artificial Sequence
<220> FEATURE:
<223> OTHER INFORMATION: 5'-Iodo-2'-deoxyuridine
<220> FEATURE:
<221> NAME/KEY: modified_base
<222> LOCATION: (1)..(1)
<223> OTHER INFORMATION: 5'-Iodo-2'-deoxyuridine
<220> FEATURE:
<221> NAME/KEY: misc_feature
<222> LOCATION: (1)..(1)
<223> OTHER INFORMATION: n is a, c, g, or t

<400> SEQUENCE: 8
ncgtcgacga tcggcggccg ccgt                                          24

<210> SEQ ID NO 9
<211> LENGTH: 24
<212> TYPE: DNA
<213> ORGANISM: Artificial Sequence
<220> FEATURE:
<223> OTHER INFORMATION: CpG oligonucleotide
<220> FEATURE:
<221> NAME/KEY: modified_base
<222> LOCATION: (1)..(1)
<223> OTHER INFORMATION: 5'-Iodo-2'-deoxyuridine
<220> FEATURE:
<221> NAME/KEY: misc_feature
<222> LOCATION: (1)..(1)
<223> OTHER INFORMATION: n is a, c, g, or t

<400> SEQUENCE: 9
ncgtcgacga tcggcggccg ccgt                                          24
```

```
<210> SEQ ID NO 10
<211> LENGTH: 23
<212> TYPE: DNA
<213> ORGANISM: Artificial Sequence
<220> FEATURE:
<223> OTHER INFORMATION: CpG oligonucleotide

<400> SEQUENCE: 10
tcgtcgacga tcggcgcgcg ccg                                               23

<210> SEQ ID NO 11
<211> LENGTH: 20
<212> TYPE: RNA
<213> ORGANISM: Artificial Sequence
<220> FEATURE:
<223> OTHER INFORMATION: immunostimulatory oligoribonucleotide

<400> SEQUENCE: 11
uuguuguugu uguuguuguu                                                   20

<210> SEQ ID NO 12
<211> LENGTH: 20
<212> TYPE: DNA
<213> ORGANISM: Artificial Sequence
<220> FEATURE:
<223> OTHER INFORMATION: immunostimulatory oligoribonucleotide

<400> SEQUENCE: 12
uuauuauuau uauuauuauu                                                   20

<210> SEQ ID NO 13
<211> LENGTH: 19
<212> TYPE: DNA
<213> ORGANISM: Artificial Sequence
<220> FEATURE:
<223> OTHER INFORMATION: immunostimulatory oligoribonucleotide

<400> SEQUENCE: 13
aaacgcucag ccaaagcag                                                    19
```

METHODS AND COMPOSITIONS FOR INDUCTION OF IMMUNE RESPONSE

FIELD OF INVENTION

The instant invention relates to methods of using immunomodulators for inducing non-specific response to an infection.

BACKGROUND

When the body exhibits immune responses to an infectious or immunological challenge, a distinction is drawn between the innate immune response (innate immunity) and the acquired immune response (antigen-specific adaptive immunity).

The innate immune system is a highly effective and evolved general defense system. Elements of innate immunity are always present at low levels and are activated very rapidly when stimulated. Stimulation can include interaction of bacterial signaling molecules with pattern recognition receptors on the surface of the body's cells or other mechanisms of disease. Every day, animals are exposed to potentially pathogenic microorganisms through the food and water, the air and the surfaces touched. The innate immune system acts to prevent these potential pathogens from causing disease. The innate immune system differs from so-called adaptive immunity (which includes antibodies and antigen-specific B- and T-lymphocytes) because it is always present, effective immediately, and relatively non-specific for any given pathogen. The adaptive immune system requires amplification of specific recognition elements and thus takes days to weeks to respond. Even when adaptive immunity is pre-stimulated by vaccination, it may take three days or more to respond to a pathogen whereas innate immunity is immediately or rapidly (within hours) available. Innate immunity is known to involve a variety of effector functions including phagocytic cells, complement, etc., but is generally incompletely understood.

Accordingly, situations arise when activation of innate immune response is highly desirable. For example, in the field of veterinary medicine, it is particularly useful to activate the innate immune system when an animal has been or is about to be subjected to a change in environment, such as, for example, during or immediately after transportation, or in an environment where individual animals are in close proximity, whereby the spread of the pathogen is potentially rapid.

SUMMARY OF INVENTION

The instant invention provides methods and compositions for the activation of innate immune system. In certain aspects, the invention provides a substantially antigen-free composition comprising (or, in certain embodiments, consisting essentially, or consisting of) a saponin, a sterol, a quaternary amine, and a polyacrylic polymer, and optionally, at least one of a glycolipid and an immunostimulatory oligonucleotide, for use in induction of an immune response in a mammal or a bird. In certain embodiments, the composition may be antigen-free.

In certain aspects the invention provides a method of inducing an immune response in an animal, comprising administering to said animal a substantially antigen-free composition comprising a saponin, the sterol, the quaternary amine, and the polyacrylic polymer, wherein said animal is selected from the group consisting of mammals and birds. In some embodiments, the composition may be antigen-free.

In certain aspects, the compositions recited above further comprise a glycolipid, an immunostimulatory oligonucleotide or both the glycolipid and the immunostimulatory oligonucleotide.

In embodiments applicable to each of the aspects set out above, the saponin is present in the amount of between about 1 µg to about 5,000 µg per dose (preferably, between about 10 and about 50 µg per dose), the sterol is present in the amount of 1 µg to about 5,000 µg per dose (preferably, between about 10 and about 50 µg per dose), the quaternary amine compound is present in the amount of 1 µg to about 5,000 µg per dose (preferably, between about 1 and about 30 µg per dose), and the polyacrylic polymer is present in the amount of 0.0001% v/v to about 75% v/v per dose (preferably between about 0.01 and 0.1% v/v per dose). If the glycolipid is present, its amount is typically between about 0.01 mg to about 10 mg per dose (preferably about 1 mg to about 2 mg per dose). If the immunostimulatory oligonucleotide is present, its amount typically ranges between 20 µg to about 500 µg per ml (preferably about 100 µg per ml to about 200 µg per ml).

The compositions of the instant invention may be used to trigger protective immune response to a challenge by multiple organisms such as viruses, Gram-positive, and Gram-negative bacteria. In certain embodiments, the compositions of the instant invention are used to trigger a protective immune response to Gram-negative bacteria such as *Bordetella bronchiseptica*.

DETAILED DESCRIPTION OF SELECTED EMBODIMENTS

In order to assist a person of ordinary skill in the art in the understanding of the instant invention, the following non-limiting definitions are provided.

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

"Alkyl" refers to both straight and branched saturated hydrocarbon moieties.

"Amine" refers to a chemical compound derived from ammonia by substituting hydrocarbon groups for one or more hydrogen atoms. "Quaternary amine" refers to an ammonium based compound with four hydrocarbon groups.

"Antigen" refers to any substance that stimulates a specific immune response. The term includes killed, inactivated, attenuated, or modified live bacteria, viruses, or parasites. The term antigen also includes polynucleotides, polypeptides, recombinant proteins, synthetic peptides, protein extract, cells (including tumor cells), tissues, polysaccharides, or lipids, or fragments thereof, individually or in any combination thereof. The term antigen also includes antibodies, such as anti-idiotype antibodies or fragments thereof, and to synthetic peptide mimotopes that can mimic an antigen or antigenic determinant (epitope).

"Consisting essentially" as applied to adjuvant formulations refers to a formulation which does not contain unrecited additional adjuvanting or immunomodulating agents in the amounts at which such agents exert measurable adjuvanting or immunomodulating effects.

"Dose" refers to a unit of composition given to a subject, and may be a unit of mass or a unit of volume.

"Immunostimulatory molecule" refers to a molecule that generates an immune response.

"Parenteral administration" refers to the introduction of a substance, such as a vaccine, into a subject's body through or by way of a route that does not include the digestive tract. Parenteral administration includes subcutaneous, intramuscular, transcutaneous, intradermal, intraperitoneal, intraocular, and intravenous administration.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

"Saponin" refers to a group of surface-active glycosides of plant origin composed of a hydrophilic region (usually several sugar chains) in association with a hydrophobic region of either steroid or triterpenoid structure.

"Steroids" refers to any of a group of organic compounds belonging to biochemical class of lipids, comprising a four-fused ring system of three fused cyclohexane (six-carbon) rings plus a fourth cyclopentane (five-carbon) ring. Steroids are typically highly in soluble inorganic solvents and slightly soluble in water.

"Sterols" refers to compounds in animals which are biologically produced from terpenoid precursors. They comprise a steroid ring structure, having a hydroxyl (OH) group, usually attached to carbon-3. The hydrocarbon chain of the fatty-acid substituent varies in length, usually from 16 to 20 carbon atoms, and can be saturated or unsaturated. Sterols commonly contain one or more double bonds in the ring structure and also a variety of substituents attached to the rings. Sterols and their fatty-acid esters are essentially water insoluble.

"Substantially antigen-free composition" refers to a composition wherein the amount of the antigen is insufficient to generate a protective specific immune response or to stop successful reproduction and/or expulsion (e.g., viral shedding) of the pathogen against which the specific immune response is generated by the antigen. In some embodiments, the amount of the antigen in the substantially antigen free composition is not detectable by a serological assay such as for example ELISA.

"Triterpeniods" refers to a large and diverse class of naturally occurring organic molecules, derived from six five-carbon isoprene (2-methyl-1,3-butadiene) units. Most triterpenoids are multicyclic structures which differ from one another in functional groups and in their basic carbon skeletons.

As described herein, the inventors have surprisingly discovered that compositions containing a saponin, sterol, quaternary ammonium compound, polyacrylic polymer, and, optionally, one or both of a glycolipid and/or immunostimulatory oligonucleotide are capable of triggering a protective immune response in warm-blooded animals (mammals and birds) in the absence of an antigen.

Although warm-blooded animals, i.e., mammals and birds, are capable of mounting both an innate immune response and a slower-acting, adaptive immune response, they rely primarily on their highly-developed adaptive immune mechanisms. Invertebrates, by comparison, lack adaptive immune mechanisms and thus rely completely on innate immune mechanisms. Cold-blooded vertebrates, e.g., fish, include both innate and adaptive immune response mechanisms. Compared to warm-blooded vertebrates, however, the adaptive immune response of cold-blooded vertebrates is relatively undeveloped, whereas the innate immune response of cold-blooded vertebrates is relatively highly developed. Cold-blooded vertebrates thus generally rely more on innate immune mechanisms than adaptive immune mechanisms, compared to warm-blooded animals. Because of the differences in the relative development and reliance on the innate immune system in invertebrates and cold-blooded vertebrates, compared to warm-blooded animals, results and findings concerning the respective innate immune systems of invertebrates and cold-blooded vertebrates cannot be predictably applied to the innate immune systems of warm-blooded vertebrates. In the particular, a finds that a compound or composition can stimulate the innate immune system of invertebrates or cold-blooded vertebrates is not a reasonable predictor that the compound or composition would be useful for stimulation of the innate immune system of a warm-blooded mammal.

The innate immune system is a rapidly deployed, highly effective general defense system can afford protection against pathogenic agents. It is therefore desirable to identify compounds and compositions that stimulate or improve the innate immune response system in warm-blooded vertebrates. As described herein, the inventors have surprisingly discovered that compositions containing a saponin, sterol, quaternary ammonium compound, polyacrylic polymer and, optionally, one or both of a glycolipid and/or immunostimulatory oligonucleotide, (referred to as QCDC, QCDCR, QCDCT, and QCDCRT, respectively) effectively activate the innate immune system of warm-blooded animals and may be used as immunomodulators, i.e., independently of the antigen, to improve an immune response to a challenge in warm-blooded animals (e.g., mammals and birds). The finding that the QCDC, QCDCR, QCDCT, and QCDCRT compositions described herein are sufficiently potent to effectively activate less versatile innate immune system of warm-blooded animals was surprising and unexpected.

Therefore, in certain embodiments, the invention provides a composition for improving an immune response in a mammal or a bird, the composition comprising a sterol, a saponin, a quaternary amine, a polyacrylic polymer, such as, for example, CARBOPOL®. This four-component composition is referred to as QCDC. The QCDC composition may also contain a glycolipid (R), an immunostimulatory oligonucleotide (T), or both.

Sterols share a common chemical core, which is a steroid ring structure[s], having a hydroxyl (OH) group, usually attached to carbon-3. The hydrocarbon chain of the fatty-acid substituent varies in length, usually from 16 to 20 carbon atoms, and can be saturated or unsaturated. Sterols commonly contain one or more double bonds in the ring structure and also a variety of substituents attached to the rings. Sterols and their corresponding fatty-acid esters are essentially water insoluble. In view of these chemical similarities, it is thus likely that the sterols sharing this chemical core would have similar properties when used in the vaccine compositions of the instant invention. Sterols are well known in the art and can be purchased commercially. For example cholesterol is disclosed in the Merck Index, 12th Ed., p. 369. Suitable sterols include, without limitations, β-sitosterol, stigmasterol, ergosterol, ergocalciferol, and cholesterol.

Sterols are generally used in an amount of about 1 µg to about 5,000 µg per dose. They also are used in an amount of about 1 µg to about 4,000 µg per dose, about 1 µg to about 3,000 µg per dose, about 1 µg to about 2,000 µg per dose, and about 1 µg to about 1,000 µg per dose. They are also used in an amount of about 5 µg to about 750 µg per dose, about 5 µg to about 500 µg per dose, about 5 µg to about 200 µg per dose, about 5 µg to about 100 µg per dose, about 15 µg to about 100 µg per dose, and about 15 µg to about 30 µg per dose.

Suitable saponins include triterpenoid saponins. These triterpenoids a group of surface-active glycosides of plant origin and share common chemical core composed of a hydrophilic region (usually several sugar chains) in association with a hydrophobic region of either steroid or triterpenoid structure. Because of these similarities, the saponins sharing this chemical core are likely to have similar adjuvanting properties. Triterpenoids suitable for use in the adjuvant compositions can come from many sources, either plant derived or synthetic equivalents, including but not limited to, *Quillaja saponaria*, tomatine, ginseng extracts, mushrooms, and an alkaloid glycoside structurally similar to steroidal saponins. Thus, triterpenoids suitable for use in the adjuvant compositions include saponins, squalene, and lanosterol. In other set of embodiments, the saponin may be, for example, Quil A or another purified or partially purified saponin preparation, which can be obtained commercially. Thus, saponin extracts can be used as mixtures or purified individual components such as QS-7, QS-17, QS-18, and QS-21. In one embodiment the Quil A is at least 85% pure. In certain embodiments, the Quil A is at least 90%, 91%, 92%, 93%, 94%, 95%, 96%, 97%, 98%, or 99% pure.

A saponin may be present in the compositions of the instant invention in the amount of about 1 µg to about 5,000 µg per dose. They also are used in an amount of about 1 µg to about 4,000 µg per dose, about 1 µg to about 3,000 µg per dose, about 1 µg to about 2,000 µg per dose, and about 1 µg to about 1,000 µg per dose. They are also used in an amount of about 5 µg to about 750 µg per dose, about 5 µg to about 500 µg per dose, about 5 µg to about 200 µg per dose, about 5 µg to about 100 µg per dose, about 15 µg to about 100 µg per dose, and in an amount of about 15 µg to about 30 µg per dose.

Quaternary amine compounds are ammonium based compounds with four hydrocarbon groups. Such hydrocarbon groups are generally limited to alkyl or aryl groups. In certain embodiments, the quaternary amine compounds are composed of four alkyl chains, two of which are $C_{10}$-$C_{20}$ alkyls and the remaining two are $C_1$-$C_4$ alkyls. In one set of embodiments, the quaternary amine is Didecyldimethylammonium (DDA). In certain embodiments, avridine may be used.

A quaternary amine may be present in the compositions of the instant invention in the amount of about 1 µg to about 5,000 µg per dose. They also are used in an amount of about 1 µg to about 4,000 µg per dose, about 1 µg to about 3,000 µg per dose, about 1 µg to about 2,000 µg per dose, and about 1 µg to about 1,000 µg per dose. They are also used in an amount of about 5 µg to about 750 µg per dose, about 5 µg to about 500 µg per dose, about 5 µg to about 200 µg per dose, about 5 µg to about 100 µg per dose, about 15 µg to about 100 µg per dose, and in an amount of about 15 µg to about 30 µg per dose. As a specific example, adjuvant compositions containing DDA can be prepared by simply mixing an antigen solution with a freshly prepared solution of DDA.

Multiple polyacrylic polymers suitable for use in the instant invention are commercially available. In certain embodiments, the polyacrylic polymer includes polyacrylic acid, which is commercially available under the trade name CARBOPOL®. These polymers have an average equivalent weight of 76. They are produced from primary polymer particles of about 0.2 to 6.0 microns in average diameter. The CARBOPOL® polymers swell in water up to 1000 times their original volume and ten times their original diameter to form a gel when exposed to a pH environment greater than the pKa of the carboxylate group. At a pH greater than the pKa of carboxylate group, the carboxylate groups ionize resulting in repulsion between the negative charges, which adds to the swelling of the polymer.

A polyacrylic polymer may be present in the compositions of the instant invention in the amount of about 0.0001% volume to volume (v/v) to about 75% v/v. In certain embodiments, it is used in an amount of about 0.001% v/v to about 50% v/v, of about 0.005% v/v to about 25% v/v, of about 0.01% v/v to about 10% v/v, of about 0.05% v/v to about 2% v/v. In another embodiment, it is used in an amount of about 0.02 v/v to about 0.1% v/v.

Suitable glycolipids are generally those which activate the Th2 response. Examples of glycolipids include, without limitation, compounds encompassed by Formula I and that are generally described in US Publication 20070196384 (Ramasamy et al.).

Formula I

In the structure of Formula I, $R^1$ is hydrogen, or a saturated alkyl radical having up to 20 carbon atoms; X is $-CH_2-$, $-O-$ or $-NH-$; $R^2$ is hydrogen, or a saturated or unsaturated alkyl radical having up to 20 carbon atoms; $R^3$, $R^4$, and $R^5$ are independently hydrogen, $-SO_4^{2-}$, $-PO_4^{2-}$, $-COC_{1-10}$ alkyl; $R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers.

In certain embodiments, the suitable glycolipid is N-(2-Deoxy-2-L-leucylamino-b-D-glucopyranosyl)-N-octadecyl-dodecanoylamide or a salt thereof. In certain embodiments, the salt is an acetate salt.

In certain embodiments, the glycolipid is present in the compositions of the instant invention in the amount of about 0.01 mg to about 10 mg per dose. In certain embodiments, they are used in an amount of about 0.05 mg to about 7.5 mg per dose, of about 0.05 mg to about 1 mg per dose, of about 0.5 mg to about 2.5 mg per dose, and of 1 mg to about 2 mg per dose.

Immunostimulatory oligonucleotides may also be used in certain embodiments of this invention, in combination with QCDC or QCDCR. Generally, immunostimulatory oligonucleotides contain at least one CG motif, and sometimes are referred to as CpG nucleotides. CpG oligonucleotides are characterized by the presence of an unmethylated CG dinucleotide in specific base-sequence contexts (CpG motif). (Hansel T T, Barnes P J (eds): New Drugs for Asthma, Allergy and COPD. Prog Respir Res. Basel, Karger, 2001, vol 31, pp 229-232, which is incorporated herein by reference). CpG motifs are present in bacterial DNA, to which they confer immunostimulatory properties. CpG motifs are typically not found in eukaryotic DNA, in which CG dinucleotides are suppressed and, when present, are usually methylated.

The adjuvants of the instant invention may include a so-called P-class immunostimulatory oligonucleotide, including, for example, a modified P-class immunostimulatory oligonucleotides. P-class immunostimulatory oligonucleotides are CpG oligonucleotides characterized by the presence of palindromes, generally 6-20 nucleotides long. The presence of such palindromes allows for possible formation of concatamers or stem-and-loop structures. The overall length of P-class immunostimulatory oligonucleotides is typically between 19 and 100 nucleotides, e.g., 19-30 nucleotides, 30-40 nucleotides, 40-50 nucleotides, 50-60 nucleotides, 60-70 nucleotides, 70-80 nucleotides, 80-90 nucleotides, 90-100 nucleotides.

In certain aspects of the invention the immunostimulatory oligonucleotide contains a 5' TLR activation domain and at least two palindromic regions, one palindromic region being a 5' palindromic region of at least 6 nucleotides in length and connected to a 3' palindromic region of at least 8 nucleotides in length either directly or through a spacer.

The P-class immunostimulatory oligonucleotides may be modified according to techniques known in the art. For example, J-modification refers to iodo-modified nucleotides. E-modification refers to ethyl-modified nucleotide(s). Thus, E-modified P-class immunostimulatory oligonucleotides are P-class immunostimulatory oligonucleotides, wherein at least one nucleotide (preferably 5' nucleotide) is ethylated. Additional modifications include attachment of 6-nitro-benzimidazol, O-Methylation, modification with proynyl-dU, inosine modification, 2-bromovinyl attachment (preferably to uridine).

The P-class immunostimulatory oligonucleotides may also contain a modified internucleotide linkage including, without limitations, phosphodiester linkages and phosphorothioate linkages. Oligonucleotides may be synthesized or obtained from commercial sources.

Examples of P-Class oligonucleotides and modified P-class oligonucleotides are disclosed in published PCT application no. WO2008/068638, published on Jun. 12, 2008. Suitable non-limiting examples of modified P-class immunostimulatory oligonucleotides are provided below (In SEQ ID NOs 1-10, "*" refers to a phosphorothioate bond and "—" refers to a phosphodiester bond; in SEQ ID NOs 11-13 all bonds are phosphodiester bonds).

```
                                              SEQ ID NO: 1
5' T*C-G*T*C-G*A*C-G*A*T*C-G*G*C*G*C-G*C*G*C*C*G
3'
                                              SEQ ID NO: 2
5' T*C-G*A*C*G*T*C*G*A*T*C*G*G*C*G*C*G*C*G*C*C*G
3'
                                              SEQ ID NO: 3
5' T*C*G*A*C*G*T*C*G*A*T*C*G*G*C*G*C*G*C*G*C*C*G*T
3'
```

```
                                              SEQ ID NO: 4
5' JU*C-G*A*C*G*T*C*G*A*T*C*G*G*C*G*C*G*C*G*C*C*G
3'
                                              SEQ ID NO: 5
5' JU*C-G*A*C*G*T*C*G*A*T*C*G*G*C*G*C*G*C*G*C*C*
G*T 3'
                                              SEQ ID NO: 6
5' JU*C*G*A*C*G*T*C*G*A*T*C*G*G*C*G*C*G*C*G*C*C*
G*T 3'
                                              SEQ ID NO: 7
5' EU*C-G*A*C*G*T*C*G*A*T*C*G*G*C*G*C*G*C*G*C*C*G
3'
                                              SEQ ID NO: 8
5' JU*C-G*T*C*G*A*C*G*A*T*C*G*G*C*G*C*C*G*C*C*
G*T 3'
                                              SEQ ID NO: 9
5' JU*C*G*T*C*G*A*C*G*A*T*C*G*G*C*G*G*C*C*G*C*C*
G*T 3'
                                              SEQ ID NO: 10
5' T*C-G*T*C-G*A*C-G*A*T*C-G*G*C*G*C-G*C*G*C*C*G
3'
                                              SEQ ID NO: 11
5'-UUGUUGUUGUUGUUGUUGUU-3'
                                              SEQ ID NO: 12
5'-UUAUUAUUAUUAUUAUUAUU-3'
                                              SEQ ID NO: 13
5'-AAACGCUCAGCCAAAGCAG-3'.
```

P-class immunostimulatory oligonucleotides are generally used in the adjuvant compositions described herein in an amount of about 20 µg to about 500 µg per ml. They also are used in an amount of about 25 µg to about 400 mg per ml, about 40 µg to about 250 µg per ml, about 50 µg to about 200 µg per ml, about 100 µg per ml to about 200 µg per ml.

Methods of making the compositions described herein are described in, e.g., US Publication 20090324641 (Dominowski et al, published on Dec. 31, 2009). Briefly, the compounds of the composition may be admixed together, preferably, with the polyacrylic polymer added last. The compositions may be microfluidized prior to the addition of the polyacrylic polymer.

The compositions described herein generally did not require any specific carrier, and can be formulated in an aqueous or other pharmaceutically acceptable buffer. The adjuvant compositions can be made in various forms depending upon the route of administration, storage requirements, and the like. For example, they can be made in the form of sterile aqueous solutions or dispersions suitable for injectable use, or made in lyophilized forms using freeze-drying, vacuum-drying, or spray-drying techniques. Lyophilized compositions can be reconstituted prior to use in a stabilizing solution, e.g., saline or HEPES. Thus, the adjuvant compositions can be used as a solid, semi-solid, or liquid dosage form.

Phosphate buffered saline (PBS) may be used as an aqueous buffer medium; the pH of the buffer may be neutral or slightly alkaline or slightly acidic. Accordingly, the pH can be in a range of pH 6 to 8. A pH of about 7.0 to about 7.3 is common. The strength of the buffer can be between 10 to 50 mM $PO_4$ and between 10 to 150 mM $PO_4$. In one example, 0.063% PBS is used. The pH can be adjusted using NaOH or HCl as needed. Typical concentrations include from 1N to 10N HCl and 1N to 10N NaOH.

Compositions can be homogenized or microfluidized. The compositions are subjected to a primary blending process, typically by passage one or more times through one or more homogenizers. Any commercially available homogenizer can be used for this purpose, e.g., Ross emulsifier (Hauppauge, N.Y.), Gaulin homogenizer (Everett, Mass.), or Microfluidics (Newton, Mass.).

In certain embodiments, a saponin is added to an appropriate buffer. A sterol is then slowly added to the saponin solution, followed by the slow addition of a quaternary ammonium compound. If present, the glycolipid and/or the immunostimulatory oligonucleotide are also added. The resulting composition is homogenized, and then microfluidized. After microfluidization, a polymer is added to microfluidized composition. Depending on the components used, the order of these steps can be altered to optimize preparation of the compositions.

In one embodiment, the compositions are homogenized for three minutes at 10,000 rpm. Microfluidization can be achieved by use of a commercial microfluidizer, such as model number 110Y available from Microfluidics, (Newton, Mass.); Gaulin Model 30CD (Gaulin, Inc., Everett, Mass.); and Rainnie Minilab Type 8.30H (Miro Atomizer Food and Dairy, Inc., Hudson, Wis.). These microfluidizers operate by forcing fluids through small apertures under high pressure, such that two fluid streams interact at high velocities in an interaction chamber to form compositions with droplets of a submicron size. In one embodiment, the formulations are microfluidized by being passed through a 200 micron limiting dimension chamber at 10,000±500 psi.

Dose sizes of the compositions typically range from about 0.05 mL to about 5 mL, inclusive, depending on the subject and the antigen. For example, for a canine or feline, a dose of about 1 mL is typically used, while in cattle a dose of about 2-5 mL is typically used. However, these adjuvants also can be formulated in microdoses, wherein doses of about 100 μL can be used, e.g., for administration to chicken.

Routes of administration for adjuvant compositions include parenteral, oral, oronasal, intranasal, intratracheal, topical, and in ova. Any suitable device may be used to administer the compositions, including syringes, droppers, needleless injection devices, patches, and the like. The route and device selected for use will depend on the ingredients of the composition and the size of the animal.

Different mammals and birds are suitable for treatment by the methods of the instant invention. Such animals include, without limitations, dogs, cats, horses, sheep, bovines, swine, geese, chicken, ducks, etc.

An advantageous aspect of the instant invention is that it can be administered to the subject mammal or bird when the immune system of the animal is weakened, when the animal is in a high-stress environment, or there is a high potential for exposure to pathogens. For example, animals may be treated immediately before or during transportation, or immediately after transportation when they are quarantined. Sometimes, suitable antigens are not easily available, or even unknown.

If a disease is known to present itself in a rapid onset, activation of innate immune system is particularly important. Also, this invention may be used in animals which are housed in crowded environment, e.g., chicken farms.

The disease may be caused by such broad classes of pathogens as viruses, Gram-positive bacteria, and Gram-negative bacteria.

Viruses include, without limitation, Avian herpesvirus, Bovine herpesviruses, Canine herpesviruses, Equine herpesviruses, Feline viral rhinotracheitis virus, Marek's disease virus, Ovine herpesviruses, Porcine herpesviruses, Pseudorabies virus, Avian paramyxoviruses, Bovine respiratory syncytial virus, Canine distemper virus, Canine parainfluenza virus, canine adenovirus, canine parvovirus, Bovine Parainfluenza virus 3, Ovine parainfluenza 3, Rinderpest virus, Border disease virus, Bovine viral diarrhea virus (BVDV), BVDV Type I, BVDV Type II, Classical swine fever virus, Avian Leukosis virus, Bovine immunodeficiency virus, Bovine leukemia virus, Bovine tuberculosis, Equine infectious anemia virus, Feline immunodeficiency virus, Feline leukemia virus (FeLV), Newcastle Disease virus, Ovine progressive pneumonia virus, Ovine pulmonary adenocarcinoma virus, Canine coronavirus (CCV), pantropic CCV, Canine respiratory coronavirus, Bovine coronavirus, Feline Calicivirus, Feline enteric coronavirus, Feline infectious peritonitis, virus, Porcine epidemic diarrhea virus, Porcine hemagglutinating encephalomyletitis virus, Porcine parvovirus, Porcine Circovirus (PCV) Type I, PCV Type II, Porcine Reproductive and Respiratory Syndrome (PRRS) Virus, Transmissible gastroenteritis virus, Turkey coronavirus, Bovine ephemeral fever virus, Rabies, Rotovirus, Vesicular stomatitis virus, lentivirus, Avian influenza, Rhinoviruses, Equine influenza virus, Swine influenza virus, Canine influenza virus, Feline influenza virus, Human influenza virus, Eastern Equine encephalitis virus (EEE), Venezuelan equine encephalitis virus, West Nile virus, Western equine encephalitis virus, human immunodeficiency virus, human papilloma virus, varicella zoster virus, hepatitis B virus, rhinovirus, and measles virus.

Gram-positive bacteria have a thick peptidoglycan layer, which is superficial to the cell membrane. Non-limiting examples of Gram-positive bacteria are streptococcal and staphylococcal bacteria. Specific examples include, without limitation, bacteria from genera *Actinomyces, Bacillus, Clostridium, Corynebacterium, Enterococcus, Listeria, Nocardia, Propionibacterium, Rhodococcus, Staphylococcus, Streptococcus*, and *Viridans*. Exemplary species include, without limitations, *S. agalactiae, S. pyogenes, S. pneumoniae, S. aureus, S. equi, C. tetani, C. botulinum, C. perfringes, C. difficile, Bacillus anthacis, Listeria monocytogenes*.

In contrast to Gram-positive bacteria, Gram-negative bacteria lack such peptidoglycan layer. The pathogenic capability of gram-negative bacteria is often associated with certain components of gram-negative cell envelope, in particular, the lipopolysaccharide layer (also known as LPS or endotoxin layer). Specific examples include, without limitations, bacteria from genera *Acinetobacter, Bordetella, Brachyspira, Burkholderia, Brucella, Cardiobacterium, Citrobacter, Coxiella, Enterobacter, Escherichia, Fusobacterium, Haemophilus, Helicobacter, Klebsiella, Legionella, Moxarella, Morganella, Neisseria, Proteus, Pseudomonas, Rickettsia, Salmonella, Serratia, Spirochaeta, Vibrio*. Exemplary species include, without limitations, *Bordetella Bronchiseptica, Brucella canis, Brucells suis, Burkhodlderia mallei, Klebsiella pneumoniae, Serratia marcescens*, and *Enterobacter cloacae*.

Parasites include, without limitations, *Anaplasma, Fasciola hepatica* (liver fluke), *Coccidia, Eimeria* spp., *Neospora caninum, Toxoplasma gondii, Giardia, Dirofilaria* (heartworms), *Ancylostoma* (hookworms), *Trypanosoma* spp., *Leishmania* spp., *Trichomonas* spp., *Cryptosporidium parvum*, *Babesia*, *Schistosoma*, *Taenia*, *Strongyloides*, *Ascaris*, *Trichinella*, *Sarcocystis*, *Hammondia*, and *Isopsora*, and combinations thereof. Also contemplated are external parasites including, but not limited to, ticks, including *Ixodes*, *Rhipicephalus*, *Dermacentor*, *Amblyomma*, *Boophilus*, *Hyalomma*, and *Haemaphysalis* species, and combinations thereof.

Fungal pathogens include *Candida*, *Microsporum*, *Aspergillus*, *Cryptococcus*, *Histoplasma*, *Pneumocystis*, *Stachybotrys*.

The following examples are presented as illustrative embodiments, but should not be taken as limiting the scope of the invention. Many changes, variations, modifications, and other uses and applications of this invention will be apparent to those skilled in the art.

EXAMPLES

Example 1: QCDC Protects Against Challenge with *B. Bronchiseptica*

Fifty Swiss Outbred CF-1 mice were randomized into two groups of 15 mice each and one group of 20 mice. Fifteen mice, approximately 18-20 g, were vaccinated with either a QAC (Quil A and Cholesterol (50 ug/50 ug per dose) in AMPHIGEN® (which is a lecithin oil emulsion), or an aqueous QCDC (Quil A/Cholesterol/DDA/CARBOPOL®; 20 ug/20 ug/10 ug/0.05%) adjuvant formulation. Each mouse received two, 0.2 ml injections, two weeks apart, by the intraperitoneal route. Twenty mice were allocated as nonvaccinated controls. Two weeks after the second injection, all three groups of mice were challenged intraperitoneally with *Bordetella bronchiseptica* strain B133.

The challenge culture was prepared as follows: briefly, the challenge organism was grown at 35-37° C. on Tryptose Blood Agar plates for approximately 24 hours. The plates were washed with a peptone saline solution, and the culture was adjusted to approximately 75% transmission at 600 nm. Each mouse received approximately $8 \times 10^7$ Colony-Forming Units of *Bordetella bronchiseptica* strain B133 by the intraperitoneal route. The number of surviving mice was tallied at seven days post-challenge.

The survival results are provided in Table 1

TABLE 1

| Treatment (N) | No. Survivors | % Survival 7 days post challenge |
|---|---|---|
| QAC (15) | 1 | 6.7 |
| QCDC (15) | 10 | 66.7 |
| Unvaccinated (20) | 4 | 20.0 |

These results suggest that treatment with QCDC without a specific antigen is sufficient to generate a protective response against Gram-negative bacteria in *B Bronchiseptica* model.

Example 2: QCDCRT Lowers Viral Titer in BHV-1 (Bovine Herpesvirus 1) Challenge in Naïve Calves The effect of formulation QCDCRT (described below) on activation of innate immune system was accessed using BHV-1 challenge in naïve calves. Animals (ten per group) that had not previously received vaccines containing BHV fractions were enrolled. Potential test animals were screened and only those with BHV serum neutralization titers less than 1:2 were selected.

Animals were acclimatized for approximately 5-7 days before challenge. During the acclimatization period, the animals were fed an antibiotic free total mixed pelleted ration. Water was provided ad libitum. Prior to arrival, animals received DECTOMAX® and DRAXXIN® per label.

The treatments are summarized in table 2 below.

TABLE 2

| Group | Treatment |
|---|---|
| T01 | Saline |
| T02 | QCDCRT-2.5 (250 µg Quil A/250 µg Cholesterol/100 µg DDA/ 0.0375% w/v CARBOPOL ®/2500 SEQ ID NO: 8/ 1000 µg BayR1005 ® |
| T03 | QCDCRT-5 (250 µg Quil A/250 µg Cholesterol/100 µg DDA/ 0.0375% w/v CARBOPOL ®/5000 SEQ ID NO: 8/ 1000 µg BayR1005 ® |
| T04 | TLR-7 agonist (proprietary) - 0.5 mg/ml in 2- Pyrrolidone:Tetraglycol 50:50% v/v |

The treatments were administered subcutaneously in 2 ml volume on day zero. BHV-1 challenge was administered intranasally (2 ml per nostril, 4 ml per animal) twelve hours after the vaccination. Prior to vaccination and at the time of challenge, blood samples and nasal swab samples were collected. Additional nasal swabs were collected daily through day 14, and additional blood sample was taken on day 14.

The amounts of IFN-alpha, MX-1 and OAS mRNA were determined by qPCR. The results obtained are summarized in FIG. 1.

Figure 1:
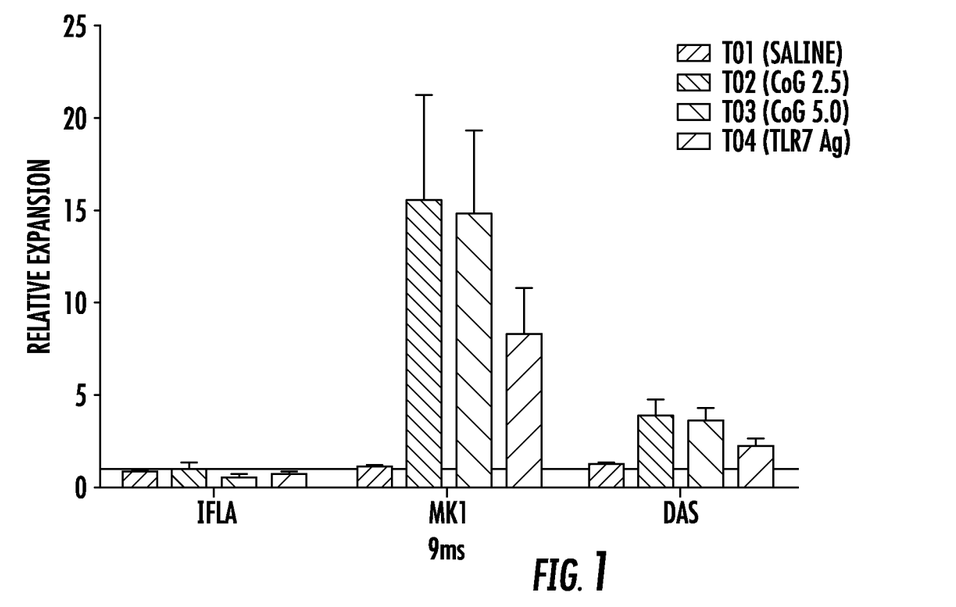
FIG. 1 illustrates the effect of QCDCRT adjuvant on IFN alpha, MX-1, and OAS mRNA levels.

The IFN-alpha levels were not significantly elevated 12 hours post-treatment. However, the levels of MX-1 and OAS mRNA showed elevation in groups T02, T03, and T04, with T02 and T03 being the most effective. Since MX-1 and OAS are downstream of IFN alpha, it is possible that IFN alpha mRNA levels might have been elevated at earlier time point.

Figure 2:
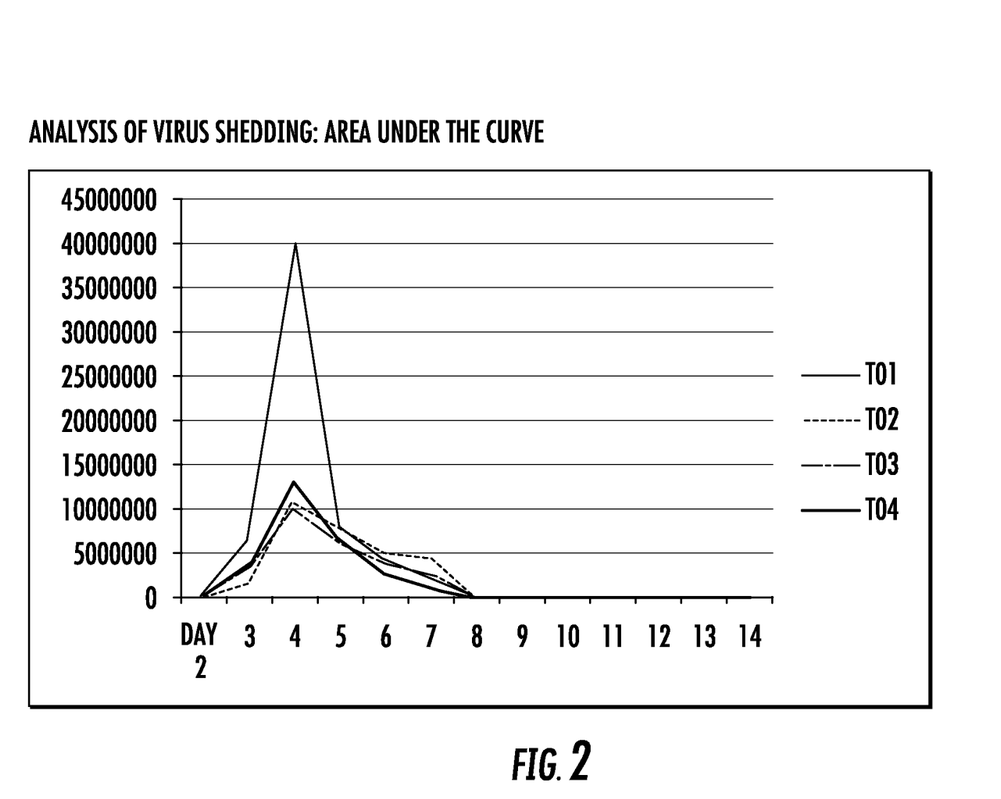
FIG. 2 illustrates effects of QCDCRT adjuvant on viral shedding in BHV-1 challenge model.

The timeline of viral shedding is illustrated in FIG. 2. Differences were observed between the control group (T01) and treatment groups (T02-T04) between days 3 and 5. In group T01 (negative control) on day 4, shedding reached a peak of about $4 \times 10^7$ units, while treatment groups it was between about 1 and $1.5 \times 10^7$ units. By day 5, the differences between the control and treatment group disappeared, and by day 9, there was no significant difference in the percent of viral shedding. All groups exhibited clinical signs of disease.

All cited publications are hereby incorporated by reference in their entirety.

While the foregoing specification teaches the principles of the present invention, with examples provided for the purpose of illustration, it will be appreciated by one skilled in the art from reading this disclosure that various changes in form and detail can be made without departing from the true scope of the invention.

The invention claimed is:

1. A method of inducing an immune response to an infection caused by Gram-negative bacteria in a mammal or bird, comprising administering, prior to exposure of said mammal or bird to said Gram-negative bacteria, a substantially antigen-free composition comprising a saponin, a sterol, a quaternary amine, and a polyacrylic polymer to the mammal or bird.

2. The method of claim 1, wherein said saponin is a triterpenoid saponin, said sterol is cholesterol, and said quaternary amine is DDA.

3. The method of claim 2, wherein said triterpenoid saponin is Quil A or a purified fraction thereof.

4. The method of claim 1, wherein the saponin is present in the amount of 1 µg to about 5,000 µg per dose, the sterol is present in the amount of 1 µg to about 5,000 µg per dose, the quaternary amine is present in the amount of 1 µg to about 5,000 µg per dose, and the polyacrylic polymer is present in the amount of 0.0001% volume to volume (v/v) to about 75% v/v.

5. The method of claim 1, wherein the composition consists essentially of the saponin, the sterol, the quaternary amine, and the polyacrylic polymer.

6. The method of claim 1, wherein said composition further comprises a glycolipid.

7. The method of claim 6, wherein the glycolipid is N-(2-Deoxy-2-L-leucylamino-b-D-glucopyranosyl)-N-octadecyldodecanoylamide or a salt thereof.

8. The method of claim 6, wherein said composition does not contain an immunostimulatory oligonucleotide.

9. The method of claim 6, wherein the composition consists essentially of the glycolipid, the saponin, the sterol, the quaternary amine, and the polyacrylic polymer.

10. The method of claim 6, wherein the glycolipid is present in the amount of 0.01 mg to about 10 mg per dose.

11. The method of claim 1, wherein the composition further comprises an immunostimulatory oligonucleotide.

12. The method of claim 11, wherein the composition consists essentially of the immunostimulatory oligonucleotide, the saponin, the sterol, the quaternary amine, and the polyacrylic polymer.

13. The method of claim 11, wherein the composition consists essentially of the immunostimulatory oligonucleotide, the glycolipid, the saponin, the sterol, the quaternary amine, and the polyacrylic polymer.

14. The method of claim 11, wherein the immunostimulatory oligonucleotide is present at the concentration of 20 µg to about 500 µg per ml.

15. The method of claim 1, wherein said Gram-negative bacteria is *Bordetella bronchiseptica*.

16. The method of claim 1, wherein said composition is antigen-free.

* * * * *